United States Patent [19]
Lal

[11] Patent Number: 5,955,150
[45] Date of Patent: Sep. 21, 1999

[54] METHOD FOR TESTING MATERIALS FOR USE IN ELECTROLESS PLATING

[75] Inventor: Sudarshan Lal, Glen Rock, N.J.

[73] Assignee: Lucent Technologies Inc., Murray Hill, N.J.

[21] Appl. No.: 08/824,026

[22] Filed: Mar. 25, 1997

Related U.S. Application Data

[63] Continuation of application No. 08/359,088, Dec. 19, 1994, abandoned.

[51] Int. Cl.$^6$ ..................................................... B05D 1/18
[52] U.S. Cl. ...................................... 427/437; 427/443.1
[58] Field of Search .................................. 427/437, 443.1

[56] References Cited

U.S. PATENT DOCUMENTS

| | | | |
|---|---|---|---|
| 4,132,605 | 1/1979 | Tench et al. ............................ | 204/1 T |
| 4,631,116 | 12/1986 | Ludwig .................................... | 204/1 T |
| 4,692,346 | 9/1987 | McBride et al. ............................ | 427/8 |
| 4,814,197 | 3/1989 | Duffy et al. .......................... | 427/443.1 |
| 4,820,643 | 4/1989 | Amelio et al. .............................. | 436/37 |
| 4,908,242 | 3/1990 | Hughes et al. ........................ | 427/443.1 |
| 5,324,399 | 6/1994 | Ludwig et al. ....................... | 204/153.1 |
| 5,384,153 | 1/1995 | Grady, Jr. et al. .......................... | 427/98 |

*Primary Examiner*—Benjamin Utech
*Attorney, Agent, or Firm*—Lester H. Birnbaum; Claude R. Narcisse

[57] ABSTRACT

Proposed is a technique for determining the suitability of use of a material for an electroless plating operation. A solution including the material is subject to an anodic linear sweep voltammetric measurement. The resulting anodic peak is compared with that of a control solution in order to evaluate the potential of the material for poisoning a factory plating bath.

7 Claims, 2 Drawing Sheets

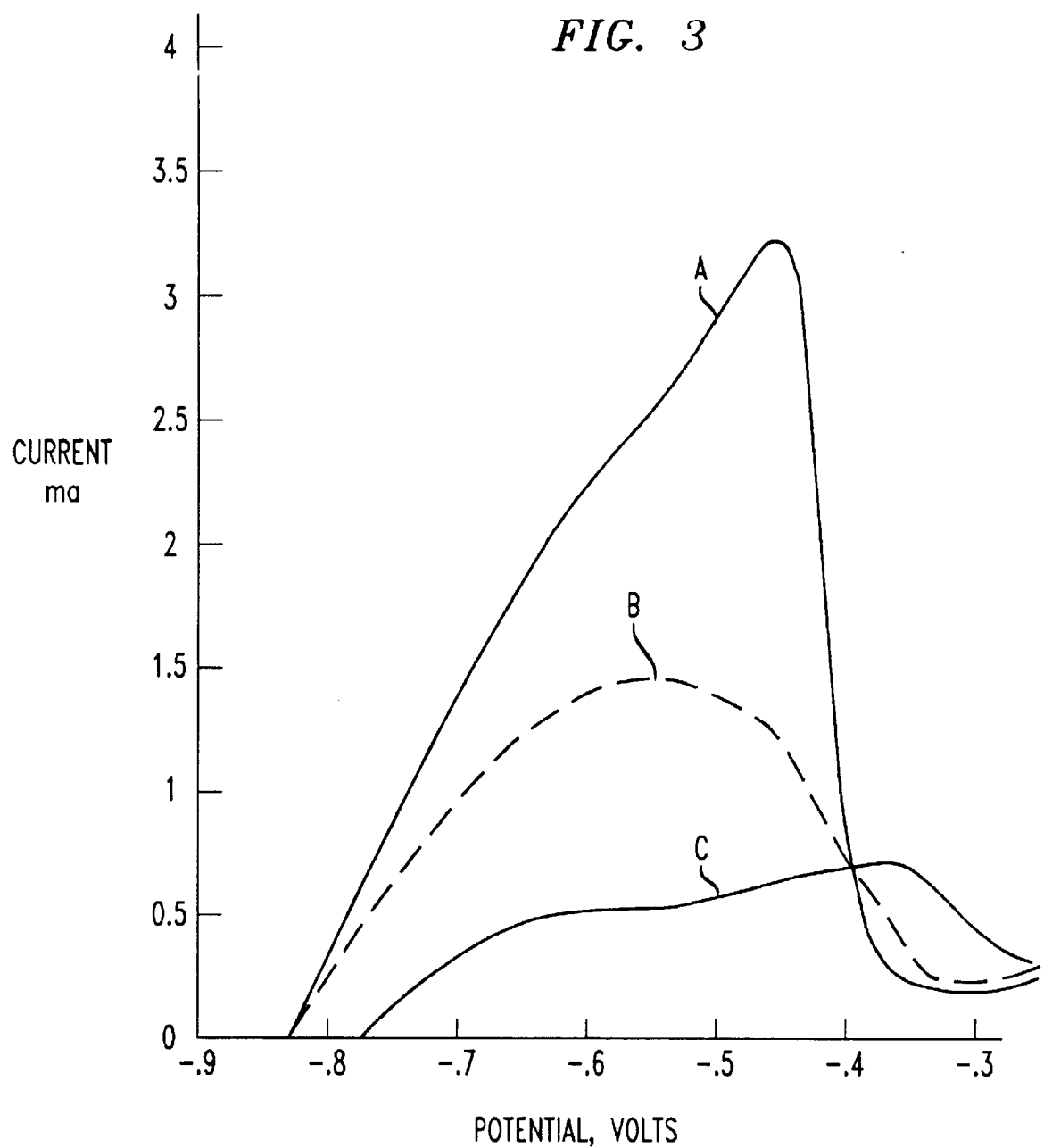

METHOD FOR TESTING MATERIALS FOR USE IN ELECTROLESS PLATING

This application is a continuation of application Ser. No. 08/359,088, filed Dec. 19, 1994, abandoned.

BACKGROUND OF THE INVENTION

This invention relates to electroless plating operations and, in particular, to a method of determining the suitability of materials for electroless plating operations.

Electroless copper plating is a significant step in the fabrication of printed circuit boards. Unfortunately, some of the components of the bath or other materials which may be inserted in the bath, such as solder masks or photoresists, may introduce contaminants. If such a contamination effect is present, it may not be detected until a plating cycle is completed, which may be several hours and result in the destruction of many circuit boards. It is desirable, therefore, to test a material before it is inserted into a factory electroless bath to determine beforehand if it is suitable for the bath.

It has been proposed to use linear sweep voltammetry to measure the ratio of anodic and cathodic reaction rates of an electroless copper plating bath, and thereby determine if the copper deposited by the bath will pass certain stress tests. (See U.S. Pat. No. 4,908,242 issued to Hughes et al.) It has also been proposed to test for contaminants in electroless baths by superimposing an AC voltage on the standard DC voltage of a voltammetric apparatus, and then sweeping the DC voltage to provide characteristic AC current spectra for a bath and comparing that spectra with the AC spectra of a known acceptable bath. (See U.S. Pat. No. 4,631,116 issued to Ludwig.) It has further been suggested to use cyclic voltammetry to determine a Pd—Sn colloid peak and compare that value to a reference in order to determine if the activity of the colloid is sufficient for subsequent electroless plating. (See U.S. Pat. No. 4,820,643 issued to Amelio et al.)

SUMMARY OF THE INVENTION

The invention is a method for electroless plating of a workpiece including determining the potential of a material for contaminating an electroless plating bath. The material is dissolved in a test bath which is placed in a voltammetric cell having at least three electrodes, and a DC voltage is supplied to two of the electrodes at an increasing rate so as to cause an anodic current at the surface of the third electrode. The resulting anodic current is measured as a function of the applied voltage to produce a current profile which is compared with a profile obtained using a second test bath of known purity.

BRIEF DESCRIPTION OF THE DRAWINGS

These and other features of the invention are delineated in detail in the following description. In the drawing:

FIG. 3 is a graph of current as a function of applied voltage for various test baths in accordance with an embodiment of the invention.

It will be appreciated that, for purposes of illustration, these figures are not necessarily drawn to scale.

DETAILED DESCRIPTION OF THE INVENTION

Figure 1:
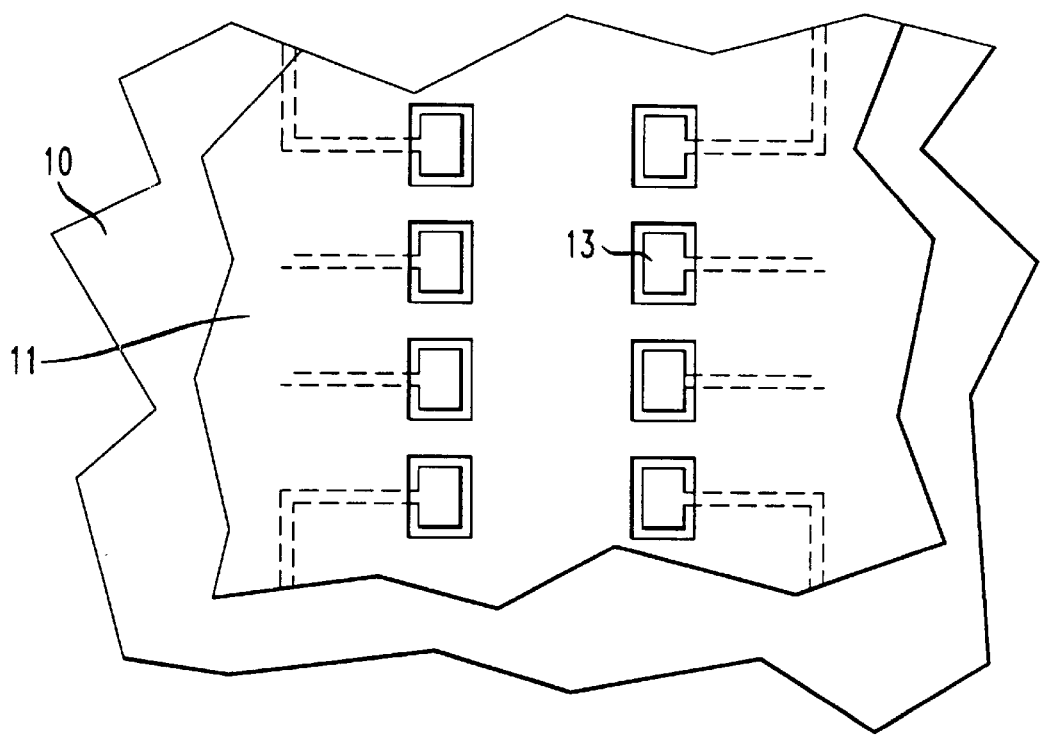
FIG. 1 is a plan view of a portion of a printed circuit board which may be electrolessly plated making use of the invention.

FIG. 1 illustrates a portion of a typical printed circuit board, 10, which is to be electrolessly plated. It will be noted that a solder mask layer, 11, covers essentially an entire major surface of the board, 10, except for conductive lands, e.g., 13, which are to be soldered in a later process. The lands are first built up by a standard electroless copper plating process. However, the solder mask material, 11, may include contaminants which can leach out during the plating process and adversely affect the plating bath. Consequently, it is desirable to determine before the plating process whether the solder mask material is suitable for such a process without contaminating the factory plating bath.

In order to test the solder mask material, a leachant solution was prepared. This involved dissolving the mask material in a modified electroless copper plating solution. In one particular example, the solder mask material was dissolved in a bath comprising a source of copper ions which was copper sulfate, a complexing agent which was ethylenediamine tetraactic acid (EDTA), and sodium hydroxide. This bath basically comprises a standard electroless copper plating bath without the reducing agent (formaldehyde) so that no plating occurs. The solder mask material was inserted in this bath for a period of approximately 18 hours while the bath was heated to a temperature of 60 degrees C. to simulate the conditions of an electroless plating operation. The result was a test solution which included a certain amount of contaminants which had leached out of the solder mask material.

Figure 2:
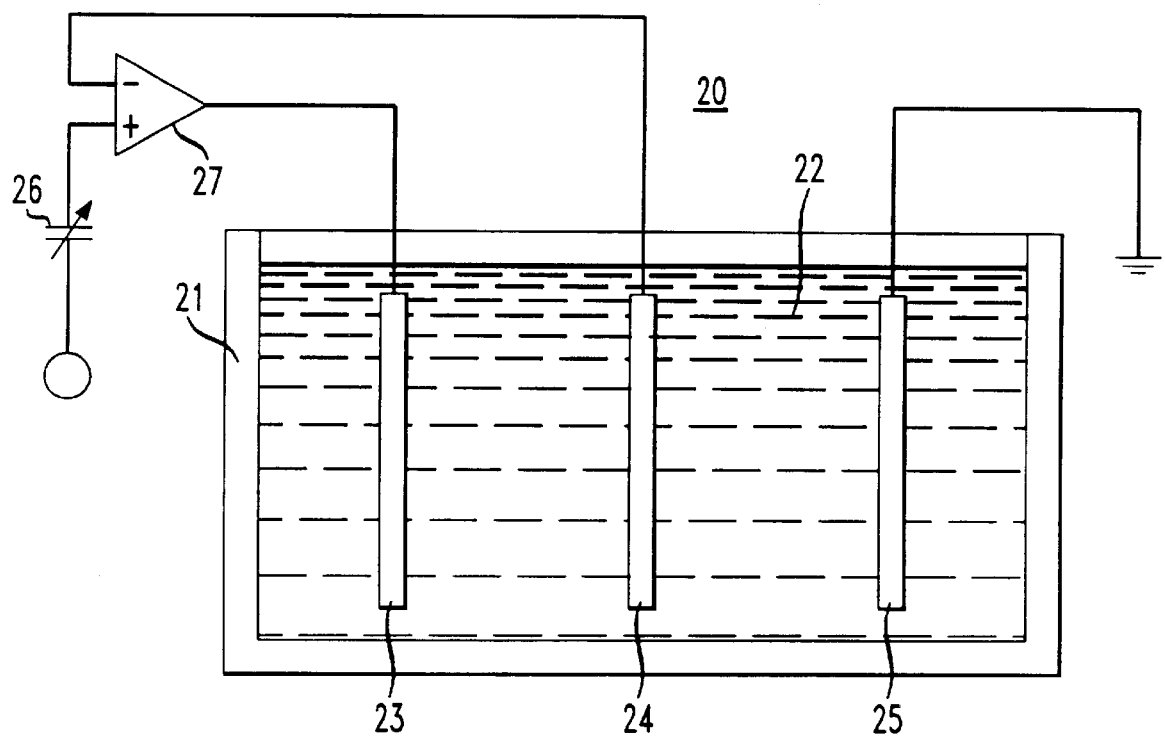
FIG. 2 is a schematic illustration of a voltammetric cell which can be used in accordance with an embodiment of the invention.

The test solution was then introduced into a voltammetric cell which is shown schematically in FIG. 2. The cell, 20, included a container, 21, for holding the test solution, 22. At least three electrodes, 23, 24 and 25, were inserted into the container, 21. Two of the electrodes, 23 and 25, were platinum with copper plated surfaces, while the third electrode, 24, constituted an Ag/AgCl reference electrode. A variable DC voltage source, 26, was coupled to the inverting input (+) of an operational amplifier, 27, whose output was coupled to one electrode, 23. The noninverting input (−) of the operational amplifier, 27, was coupled to the reference electrode, 24. The remaining electrode, 25, was coupled to a ground potential.

The variable DC voltage was applied to electrode 23 in a range known to cause anodic current in the bath, 22, due to electroless plating at the surface of the electrode 25. In this example, the voltage was varied from −0.9 to 0.2 volts at a rate of approximately 5 millivolts per second. In general, varying the voltage at a rate of 2–10 millivolts would be useful. The resulting anodic current as a function of the potential between electrode 25 and reference electrode 24 was measured and recorded as curve C in FIG. 3. This curve represents a worst case scenario for the particular solder mask material being tested.

The same procedure was followed for an electroless copper plating solution which contained components (copper sulfate, formaldehyde, EDTA, and sodium hydroxide) having a known high purity which served as a control. The anodic current as a function of potential was recorded as curve A in FIG. 3. It will be noted that curve A has a pronounced peak of approximately 3.25 milliamps while curve C from the leached solution is fairly flat. Thus, it is possible to compare the anodic peak of a test bath containing a suspect material with that of the control bath (curve A) to determine if the material in the test bath is suitable for a factory electroless plating.

Based on data obtained by comparing plating rates with the voltammetric curves, it was determined that a material would be unsuitable for use in the factory electroless plating solution if the peak of the anodic curve was less than approximately 50 percent of the control solution (curve A). Thus, the solder mask which formed the leachant solution resulting in curve C may not be usable. What remained to be done, however, was to adjust the concentration of the leachant solution to take into account the loading factor of the factory plating process, i.e., how much surface area of the material will be exposed to the plating bath.

In this example, the leachant solution was prepared with the solder mask covering a total surface area of 0.56 square meters (6 square feet) in a solution of 0.9 liters giving a loading factor of 0.62 meters squared per liter (6.67 ft$^2$/liter). A new test solution having a loading factor of only 0.0062 square meters per liter (0.067 ft$^2$/liter) was prepared by diluting 10 milliliters of the original leachant solution with 990 milliliters of the control solution. When the new solution was subjected to the voltammetric operation as previously described, the anodic current as a function of voltage shown as curve B was produced. Even at this low loading factor, the peak of the anodic curve was less than 50 percent of the control, and, consequently, the material was unsuitable.

While the invention has been described with reference to testing a solder mask material, the invention can be used to test other laminates, as well as components of the electroless bath itself. For example, if it is desired to test a new batch of formaldehyde prior to adding to the factory bath, a test bath can be prepared using other components of a known purity mixed with the formaldehyde to be tested. The test bath could then be subjected to the anodic linear sweep voltammetric process and the resulting current curve compared with that of a bath of known purity (curve A). It will also be appreciated that although a 50 percent threshold was used in the particular example described, this number may vary for particular electroless plating operations. The threshold can be determined easily by empirical methods.

I claim:

1. A method for determining the suitability of a first concentration of material for use in an electroless plating, bath comprising the steps of:

dissolving solder mask material and leaching impurities from the solder mask material to form a test bath;

placing the test bath in a voltammetric cell having at least three electrodes; supplying an increasing DC voltage two of the electrodes so as to cause anodic current at the surface of the third electrode;

measuring the anodic current resulting from the dc voltage;

recording the anodic current resulting from the dc voltage and producing a first profile of the current as a function of the supplied voltage; and comparing the first profile with a second profile obtained from a second test bath having components of a known purity.

2. A method according to claim 1 wherein the first and second profiles each have a peak value, and the peak values are compared to determine if the solder mask material is suitable for use in the electroless plating bath.

3. A method according to claim 1 wherein the electroless plating bath and the test bath comprise a source of copper.

4. A method according to claim 1 wherein an additional test bath is formed by diluting the test bath with the second test bath having components of a known purity to form a second concentration of the solder mask material, and the additional bath is placed in the voltammetric cell, an additional current profile is produced, and the additional current profile is compared with the second profile to determine the suitability of the second concentration of the solder mask material.

5. A method according to claim 1 wherein the DC voltage is varied from −0.9 to 0.2 volts.

6. A method according to claim 5 wherein the voltage is varied at a rate in the range of 2 to 10 millivolts per second.

7. A method according to claim 1 further comprising the step of electroless plating of a workpiece with the electroless plating bath including the solder mask material in the event the solder mask material is suitable based on the comparison of the first and second profiles, wherein the workpiece is a printed circuit board.

* * * * *